United States Patent
Mollet et al.

(10) Patent No.: US 6,852,523 B2
(45) Date of Patent: Feb. 8, 2005

(54) **STRAINS OF THE *BACILLUS SUBTILIS* GROUP FOR FOOD FERMENTATION**

(75) Inventors: Beat Mollet, Lausanne (CH); Raymond David Pridmore, Lausanne (CH); Marie Camille Zwahlen, Lausanne (CH)

(73) Assignee: Nestec S.A., Vevey (CH)

( * ) Notice: Subject to any disclaimer, the term of this patent is extended or adjusted under 35 U.S.C. 154(b) by 15 days.

(21) Appl. No.: 09/823,772

(22) Filed: Mar. 30, 2001

(65) Prior Publication Data

US 2002/0094329 A1 Jul. 18, 2002

Related U.S. Application Data

(63) Continuation of application No. PCT/EP99/06818, filed on Sep. 15, 1999.

(30) Foreign Application Priority Data

Oct. 2, 1998 (EP) .............................. 98118659

(51) Int. Cl.[7] .......................... C12N 1/12; C12N 15/74; A23L 1/20
(52) U.S. Cl. ...................... 435/252.31; 435/6; 435/440; 435/267; 435/471; 426/46
(58) Field of Search ........................... 435/6, 440, 471, 435/267, 252.31, 410; 426/46

(56) References Cited

U.S. PATENT DOCUMENTS

| 4,215,229 A | 7/1980 | Greco ........................ 568/804 |
| 5,476,773 A | 12/1995 | Heyland et al. ........... 435/68.1 |

FOREIGN PATENT DOCUMENTS

| EP | 0 643 922 | 3/1995 |
| JP | 55004382 B4 * | 1/1980 |
| JP | 8275772 | 10/1996 |
| JP | 9009903 | 1/1997 |

OTHER PUBLICATIONS

Ngo et al., Computational Complexity, Protein Structure Prediction, and the Levinthal Paradox, in The Protein Folding Problem and Tertiary Structure Prediction, 1994 Merz et al. (ed.), Birkhauser, Boston, MA, pp. 433 and 492–495.*

Steinkraus, K.H., et al., "Handbook of indigenous fermented food," vol. 9, pp. 530–547 (1983).

Kunst, F., et al., "The complete genome sequence of the gram positive bacterium B. subtilis," *Nature*, 390, pp. 249–256 (1997).

Mollet, B., et al., "Directed genomic integration, gene replacement, and interative gene expression in *Streptococcus thermophilus*," *Journal of Bacteriology*, 175, (14), pp. 4315–4324 (1993).

Maguin, E., et al., "Efficient insertional mutagenesis in lactococci and other gram–positive bacteria," *Journal of Bacteriology*, 178, (3), pp. 931–955 (1996).

Law, J., et al., "A system to generate chromosomal mutations in *Lactococcus lactis* which allows fast analysis of targeted genes," *Journal of Bacteriology*, 177, (24) pp. 7011–7018 (1995).

* cited by examiner

Primary Examiner—Richard Hutson
(74) Attorney, Agent, or Firm—Winston & Strawn LLP

(57) ABSTRACT

The present invention pertains to novel strains of the *Bacillus subtilis* group capable of fermenting beans, which are essentially devoid of any iso-valeric acid production. The present invention especially relates to novel strains of *Bacillus natto*, in which one or more genes involved in the biosynthetic pathway for the production of iso-valeric acids are essentially non-functional.

12 Claims, 3 Drawing Sheets

Fig 1. Schematic of the PCR reactions to construct the DNA fragment for the deletion of the *ywfL* gene in *B. natto* strain BN1.
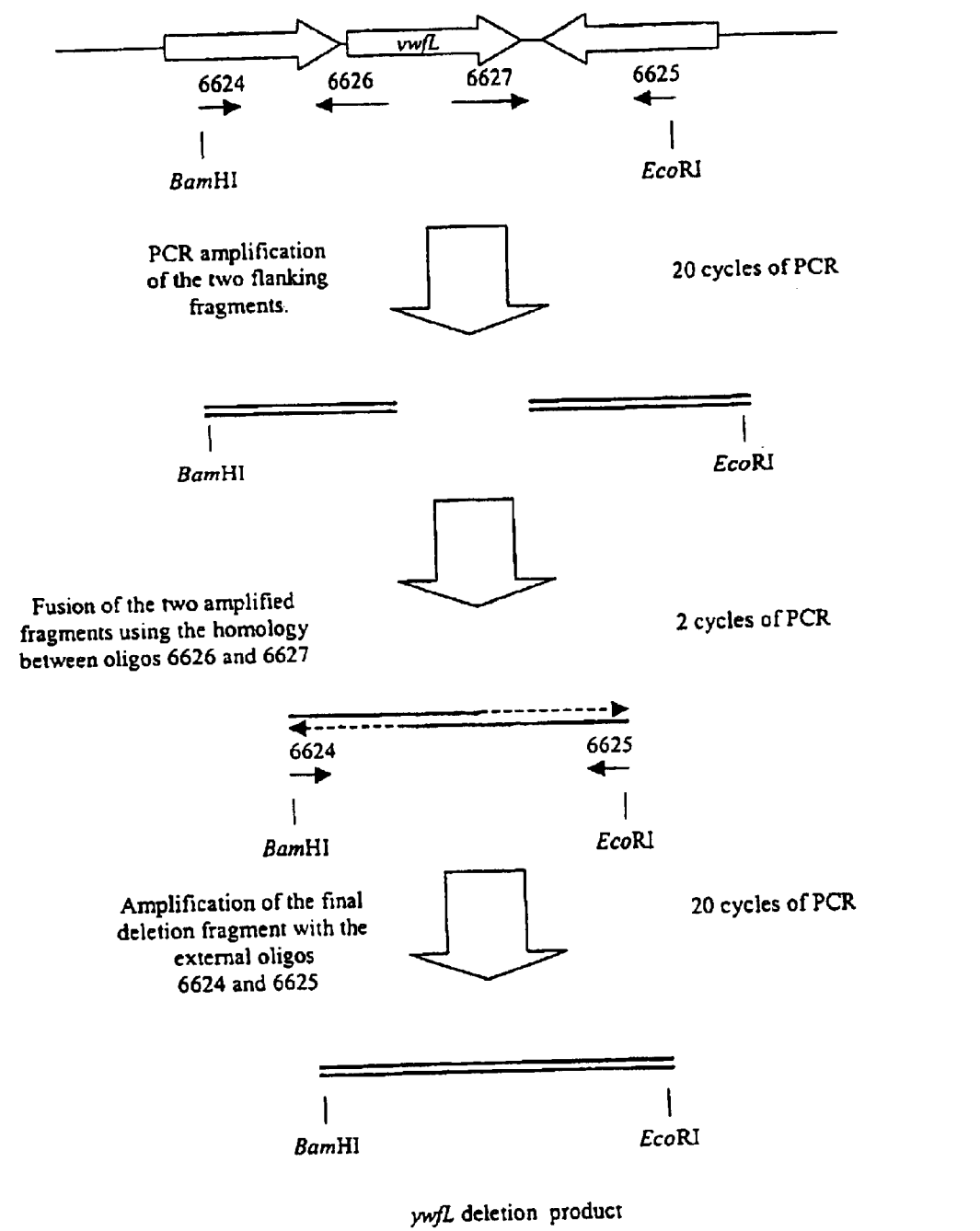

Fig. 2. Schematic map of the plasmid pMZ66.
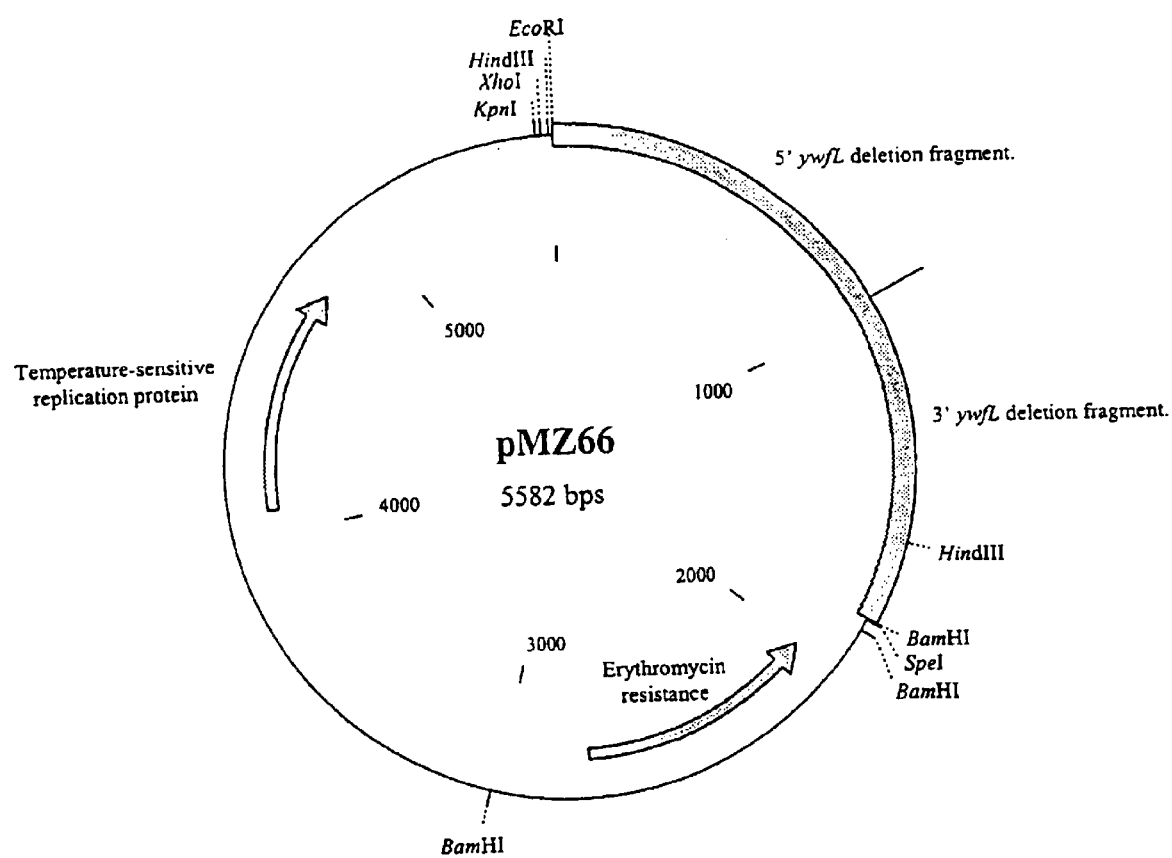

Fig. 3. Chromatogram of fermentation products in the culture medium produced by the wild-type *Bacillus natto* and the *ywfL* disruption iso-genic derivative.
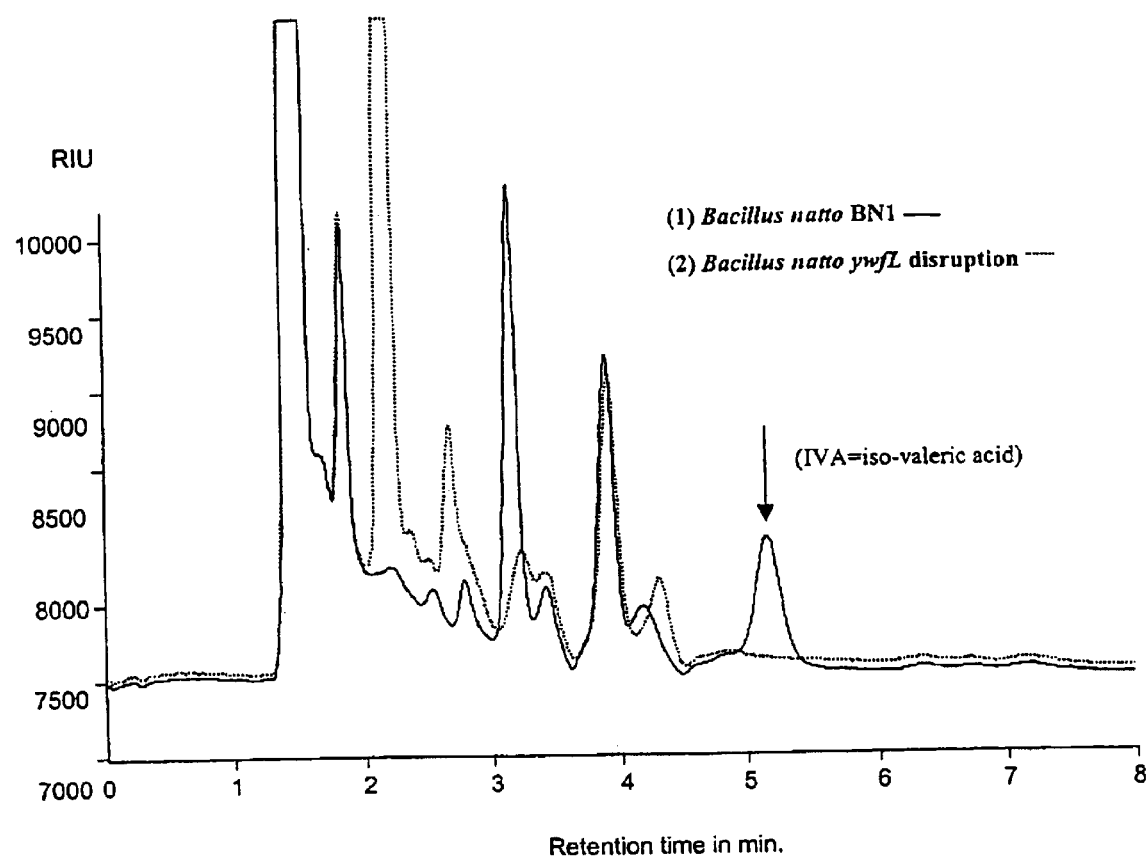

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Oligonucleotide 6624 obtained from Microsynth, Balgach, Switzerland, which introduces a BamHI restriction site approximately 950 bp upstream of the start of the ywfL gene.

<400> SEQUENCE: 1

```
                                -continued gcggcggatc cgctgatgat ctcccagcc                                      29

<210> SEQ ID NO 2
<211> LENGTH: 44
<212> TYPE: DNA
<213> ORGANISM: Bacillus subtilis

<400> SEQUENCE: 2
ctcaaattcc atttcctcat caggacatgc atagcgtatc atcc                     44

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide 6625, which introduces a EcoRI
      restriction site approximately 1000 bp downstream of the end of
      the ywfL gene.

<400> SEQUENCE: 3
ggggtcgaat tccacgagat atctaactgc c                                   31

<210> SEQ ID NO 4
<211> LENGTH: 44
<212> TYPE: DNA
<213> ORGANISM: Bacillus subtilis

<400> SEQUENCE: 4
ggatgatacg ctatgcatgt cctgatgagg aaatggaatt tgag                     44
```

STRAINS OF THE *BACILLUS SUBTILIS* GROUP FOR FOOD FERMENTATION

CROSS-REFERENCE TO RELATED APPLICATIONS

This application is a continuation of International Application No. PCT/EP99/06818, filed Sep. 15, 1999, the content of which is expressly incorporated herein by reference thereto.

TECHNICAL FIELD

The present invention pertains to novel strains of Bacillus subtilis capable of fermenting beans, which are essentially devoid of any iso-valeric acid production. The present invention especially relates to novel strains of *Bacillus natto*, in which one or more genes involved in the biosynthetic pathway for the production of iso-valeric acids are essentially non-functional.

BACKGROUND

For the production of food material, mankind has long since used various microorganisms, such as yeast, fungi or bacteria, so as to modify, prepare or change the nature or taste of foodstuffs. One such kind of microorganisms are the soil bacteria belonging to the *Bacillus subtilis* group that are used for the fermentation of different plants tissues, such as beans, e.g., soybeans and (African) locust beans, and seeds, e.g., the seeds of African oil bean, cotton seeds, melon seeds, etc. In the fermentation process, *B. subtilis* degrades cellulose and/or the protein material contained in the starting material resulting in a fermented product that may be further processed or is already ready for consumption.

One bacteria very closely related to *B. subtilis* is the so-called strain *B. natto*, a food-grade, gram-positive microorganism mainly used for the fermentation of soybeans, which fermentation process eventually results in a cheap and nutritious food that is rich in amino acids. The term *B. natto* is derived from the Japanese soybean fermented product "Natto" that is commercially produced and often eaten at breakfast (see also K. H. Steinkraus et al., Handbook of Indigenous Fermented Food, Vol. 9, (1983), 530–547).

A drawback in the fermentation of biological starting materials with microorganisms for food production resides in that a variety of by-products are generated that are not desirable by the consumer, such as an off-flavor or an unwanted hardness of the product. To this end, Japanese application no. 08-275772 describes the use of a particular strain of *B. subtilis* for reducing the amount of ammonia in the end product "Natto". This objective is achieved by keeping the protease activity during the early stage of fermentation at a high level, so that essentially all soybean proteins are degraded to a substantial degree, while in a later stage of fermentation the protease activity is remarkably reduced so as not to produce extensive amounts of ammonia which would eventually deteriorate the smell of the food product.

In Japanese application no. 09-009903, there is a described another *B. subtilis* strain that has improved hemi-cellulose degrading properties such that the end product reveals an increased softness.

Although the properties of food products derived from a fermentation with microorganisms such as *B. subtilis* have been improved in various respects, there is still a need for a further improvement of the taste and/or smell of the final end product. The present invention now satisfies that need.

SUMMARY OF THE INVENTION

The present invention relates to improving the properties of food products obtainable by a fermentation with *B. subtilis*, and especially to improving the taste thereof. This is achieved by providing a novel strain of a microorganism of the *B. subtilis* group capable of fermenting beans, preferably soybeans, which does not produce substantial amounts of iso-valeric acid. Preferably, the fermented material is essentially devoid of iso-valeric acids such that, when added to a foodstuff, no taste perceptible amounts of iso-valeric acids are present.

The invention also relates to a method for improving the flavor characteristics of a fermented plant material by fermenting the plant material with one of the bacterial strains disclosed herein so that the production of substantial amounts of iso-valeric acids are avoided. The fermented plant material can then be used to prepare a foodstuff or flavoring agent having improved flavor characteristics such as taste.

BRIEF DESCRIPTION OF THE DRAWINGS

FIG. 1 shows a flowchart for the construction of an ywfL disprution product.

FIG. 2 shows the recombinant vector pMZ66 harboring the ywfL disprution product of FIG. 1.

FIG. 3 shows a chromatogram of fermentation products produced by the wild type *Bacillus natto* and the ywfL disprution isogenic derivative.

DETAILED DESCRIPTION OF THE PREFERRED EMBODIMENTS

In the extensive experiments leading to the present invention, it has been found that the flavor of products obtainable by fermentation with *B. subtilis*, especially *B. natto*, are unfavorably affected by particular compounds produced by the microorganism during its propagation, namely certain iso-valeric acids (i.e., 2-methyl-butyric acid and 3-methyl-butyric acid), which compounds result in a clinging, strong and pungent smell of the fermentation product.

It is known that in microorganisms the major use of branched chain fatty acids, such as the iso-valeric acids, resides in the synthesis of the cell membrane where they account for approximately 90% by composition. Cell membrane synthesis is an essential function of any cell. Hence, influencing the biosynthesis of one of its components was expected to be a delicate matter, since a decreased production of any of the fatty acids required for the formation of the cell membrane or even an entire depletion thereof may eventually lead to microorganisms not viable under normal conditions or not able to fulfill their function as a fermenting agent.

Although the exact biosynthesis pathway for iso-valeric acids by *B. subtilis* is not known, a potential synthesis pathway has been devised considering the information from the newly completed total genome of *B. subtilis* (Kunst, F. et al. "The complete genome sequence of the gram positive bacterium *B. subtilis*", Nature 390 (1997), 249–256). To this end, it was also assumed that the polypeptide derived from the gene ywfL may play a vital role in the production of iso-valeric acids and similar branched chain fatty acids by the bacterium.

In the present invention, one or more genes of the subject *B. subtilis* strains involved in the biosynthesis of iso-valeric acids are rendered essentially non-functional, so that the respective gene products thereof do show a comparatively reduced activity or may essentially not be translated to the gene products at all.

In a preferred embodiment this may, e.g., be achieved by modifying one or more of the genes involved in the biosynthetic pathway for the synthesis of iso-valeric acids, preferably the ywfL gene (Nature, supra) in such a way that the gene product(s) thereof reveal merely a reduced activity, preferably a strongly reduced activity or are non-functional. These gene products may comprise polypeptides acting as enzymes within the synthesis pathway or acting as regulatory agents for the production of iso-valeric acids. In a preferred embodiment the ywfL gene may be deleted from the genome or is modified such that the gene is not transcribed into a functional protein.

In a further preferred embodiment the modified stain belonging to the B. subtilis group is of the species B. natto, most preferably B. natto BN10, that has been deposited with the Institute Pasteur under the Budapest Treaty having received the deposit number I-2077.

With respect to the objective to use the novel B. subtilis strains in foodstuff it is further preferred that no exogenous sequences, such as vector sequences or genes coding for selection markers, as e.g. antibiotic resistances, are contained in the B. subtilis strains. This applies likewise to the presence of such sequences as extra-chromosomal DNA or DNA integrated into the chromosome.

The novel strains may be obtained by known techniques, such as mutating common B. subtilis strains with known mutagens and selecting for the desired trait, that is a low or deficient synthesis of iso-valeric acids during fermentation. Mutagens and techniques for applying them are well known in the art and non-limiting examples are, e.g., DMSO (dimethylsulfoxide), MNNG (N-methyl-N'-nitro-N-nitrosoguanidine), methylamine or radiation treatment.

Moreover, the present B. subtilis strains may also be obtained by recombinant gene technology, preferably without any exogenous DNA incorporated therein, which will be described in detail hereunder.

The novel B. subtilis strains according to the invention may be used for the fermentation of plant material to eventually produce therefrom foodstuff, flavors or, more preferably, Natto. In the following the construction of a novel and stable, food-grade, genetically modified organism, B. natto, is described that contains an isogenic deletion of the chromosomal ywfL gene. This deletion has been found to be stable and contains no undesired DNA sequences, such as vector sequences or antibiotic resistance markers used for its construction. Moreover, the microorganisms obtained by deleting the ywfL gene have shown to perform equally well as compared to known B. natto strains indicating that the fermentation behavior of the novel strains are not deteriorated by the lack of the ywfL gene product.

Unless otherwise indicated, all techniques, conditions and media are as described in Sambrook et al., Molecular Cloning: A Laboratory Manual, $2^{nd}$ ed. (1992), Cold Spring Harbor Laboratory Press, NY).

Plasmids, Bacterial Strains and Media

DNA amplification of the (recombinant) E. coli vector pBS SK+ (Stratagene, product number 212205) was carried out in E. coli strain BZ234 (Mollet, B. et al. "Directed genomic integration, gene replacement, and integrative gene expression in Streptococcus thermophilus" Journal of Bacteriology 175(14) (1993), 4315–4324) while selecting for recombinant strains by means of the antibiotic ampicillin (Boehringer Mannheim, product number 835 242). Recombinant plasmids were identified with X-gal (5-bromo4-chloro-3-indolyl-β-D-galactopyranoside, Boehringer Mannheim, product number 1 680 293) and IPTG (isopropyl-β-D-thiogalactoside, Boehringer Mannheim, product number 1 411 446).

The plasmid pG+host9 (Maguin, E. et al., "Efficient insertional mutagenesis in lactococci and other gram-positive bacteria", Journal of Bacteriology 178(3) (1996), 931–935) is a gram-positive/gram-negative shuttle vector harboring a gene for the resistance to the antibiotic erythromycin (Fluka, product number E6376) and a temperature sensitive plasmid replication protein. pG+host9 is propagated in E. coli EC101 (Law, J. et al., "A system to generate chromosomal mutations in Lactococcus lactis which allows fast analysis of targeted genes", Journal of Bacteriology 177(24) (1995), 7011–7018) which provides the non-temperature sensitive replication protein integrated in the genome for convenient maintenance and amplification of the plasmid.

The B. natto strain (termed BN1) used in this work has been isolated from a fermented Natto product purchased on the market. The growth medium was LB at 37° C. for E. coli and either 28° C. or 37° C. for B. natto with agitation. Erythromycin was added to 150 μg/ml for E. coli and 2–4 μg/ml for B. natto.

B. natto Chromosomal DNA Extraction

The extraction of chromosomal DNA from B. natto for PCR and Southern blot analysis was performed on a 16 hr culture in LB medium with or without antibiotic selection as required. The culture was centrifuged at 6,000 rpm for 8 min. to pellet the bacteria. The pellet was suspended in 500 μl of 50 mM glucose, 25 mM Tris-HCl pH 8.0, 10 mM EDTA plus 500 μg/ml lysozyme (Boehringer Mannheim, 1243004) and incubated at 37° C. for 30 min. Mutanolysin (Fluka, M9901) was added to 1 μg/ml and the incubation was continued at 37° C. for another 30 min. Proteinase K was added (Fluka, P6556) to 20 μg/ml, EDTA to 2.5 mM and the cells were finally lysed by the addition of 0.1% SDS (Serva, 20763). This solution was incubated at 60° C. for 1 hr and the lysate was extracted once with an equal volume of phenol-chloroform. The mixture was centrifuged at 14,000 rpm for 8 min to separate the phases. The aqueous phase was carefully removed and the chromosomal DNA was precipitated by the addition of 2 volumes of 95% ethanol (Fluka, 02860). The DNA precipitate was spooled with a sterile toothpick, transferred to 400 μl 10 mM Tris-HCl pH 8.0, 10 mM EDTA with 50 μg/ml RNAse (Boehringer, 109 169) and incubated at 60° C. for 1 hr. The solution was phenol-chloroform extracted. The DNA was precipitated, spooled and finally suspended in 200 μl of TE buffer (10 mM Tris-HCl pH 8.0, 1 mM EDTA).

Construction of the ywfL Deletion Plasmid pMZ66

DNA fragments flanking the ywfL gene were amplified from the B. natto strain BN1 and finally combined (Fusion Cycle PCR) by their primer incorporated homologies to create a DNA fragment for the disruption of the ywfL gene in this bacterium. This is schematically shown in FIG. 1.

The 5' flanking region was amplified using th oligonucleotides 6624 (SEQ. ID. NO. 1) obtained from Microsynth, Balgach, Switzerland, which introduces a BamHi restriction site approximately 950 bp upstream of the start of the ywfL gene, and 6626 (SEQ. ID. NO. 2), a composite oligonucleotide comprising 22 bp of the sequence of the region 50 bp away from the start of the ywfL gene and 22 bp of the region 100 bp away from the end of the ywfL gene. This oligonucleotide sequence defines the region that is to be deleted, namely the sequence that is omitted between the two segments of the composite primers. This second segment from the oligonucleotide 6626 was also designed to introduce two TGA stop codons to terminate translation of the truncated ywfL gene.

The 3' flanking region was amplified using the oligonucleotides 6625 (SEQ. ID. NO. 3), which introduces a EcoRI restriction site approximately 1000 bp downstream of the end of the ywfL gene, and 6627 (SEQ. ID. NO. 4) a second composite oligonucleotide that is essentially the reverse-complement of oligonucleotide 6626 (SEQ. ID. NO. 2). These complementary oligonucleotide sequences provide the homology between the 5' and 3' fragments that is exploited in the primer-free, Pwo directed extension to complete the second strand. The two oligonucleotides 6626 and 6625 were finally added and the correct deletion fragment was specifically amplified.

The PCR reactions were carried out as follows. 500 ng of chromosomal DNA were mixed in a 100 µl volume containing 80 µl sterile $H_2O$, 6 µl 2 mM dNTPs, 10 µl Pwo polymerase reaction buffer, 2 µl each oligonucleotide at approximately 100 nM and 0.5 µl Pwo polymerase (Boehringer Mannheim, product number 1 644 947). The desired fragment was amplified using a Perkin Elmer DNA Thermal Cycler with 20 cycles of 1 min 95° C., 1 min 40° C., 2 min at 72° C. and finally held at 4° C. A 1 µl sample from each PCR reaction was prepared in a 100 µl volume containing 80 µl sterile $H_2O$, 6 µl 2 mMn dNTPs, 10 µl Pwo polymerase reaction buffer and 0.5 µl Pwo polymerase (without any oligonucleotides). This control was processed for two cycles in the Thermal Cycler as described above to extend from the oligonucleotide induced homologies. Finally, 2 µl of each oligonucleotide 6624 and 6625 at approximately 100 nM were added and the PCR reaction was continued for another 20 cycles.

The final PCR product was purified on a QIAquick PCR purification kit (Qiagen, product number 28104). A sample was digested with the restriction enzymes EcoRI and BamHI and electrophoresed on a 1% agarose gel. The corresponding 2 kb fragment was cut out of the gel and the DNA was eluted using the QIAquick gel extraction kit (Qiagen, product number 28704). The DNA fragment obtained was digested with the restriction enzymes EcoRI and BamHI and ligated with the E. coli vector pBS SK+ that has been pretreated accordingly (digested with EcoRI/BamHI and dephosphorylated). The ligation mixture was electro-transformed in the E. coli strain BZ234 and transformants were selected on LB plates supplemented with 100 µg/ml ampicillin, Xgal and IPTG. Potential positive, white colonies were screened by restriction analysis of plasmids isolated therefrom (Sambrook, supra). The DNA sequence of the insert of a positive clone was determined so as to confirm the PCR construction. This plasmid was digested with the restriction enzymes EcoRI and SpeI and the fragments were separated on a 1% agarose gel. The corresponding 2 kb fragment was cut out of the gel and the DNA was eluted using the QIAquick gel extraction kit.

The replication-temperature sensitive vector pG+Host 9 was digested with the restriction enzymes EcoRI and SpeI and the terminal phosphates were removed using shrimp alkaline phosphatase (USB, product number 70092). The ywfL deletion fragment was mixed with the pG+Host 9 vector pretreated accordingly and ligated therewith. The ligation mixture was electro-transformed into the E. coli host EC101. Colonies were screened by means of restriction analysis of isolated plasmids. One of the positive plasmids was designated pMZ66 (FIG. 2).

For the transformation into BN1, a large quantity of pMZ66 was isolated using the Jetstar Maxi prep kit (Genomed, 220010).

Transformation of B. natto

The transformation experiments were carried out according to the protocol:
Solutions:
Medium I: Spizizen's Salts 5x, 2 ml; glucose 50%, 0.1 ml; casamino acids 20%, 0.01 ml; yeast extract 5%, 0.02 ml; $MgSO_4$ 1 M, 0.05 ml; adjusted to 10 ml with distilled $H_2O$.
Medium II: Spizizen's Salts 5x, 2 ml; glucose 50%, 0.1 ml; casamino acids 20%, 0.005 ml;
$MgSO_4$ 1 M, 0.05 ml; adjusted to 10 ml with distilled $H_2O$.
Spizizen's Salts 5x: $(NH_4)_2SO_4$ 10 g, $K_2HPO_4$ 70 g, $KH_2PO_4$ 30 g, $Na_3$-citrate.$2H_2O$ 5 g,
$MgSO_4$.7 $H_2O$ 1 g, filled up with distilled $H_2O$ to 1 liter.
Natural competency of B. natto
2–3 colonies from LB plates incubated overnight at 37° C. were re-suspended into 2.5 ml of Medium I and incubated at 37° C. with aeration (240 rpm) in a sterile 10 ml glass tube for 4 to 5 hours.

Transformation of B. natto

A ten times dilution was made in Medium II (0.05 ml in 0.45 ml) with the addition of plasmid DNA (5 to 10 µg in maximum 50 µl). Incubation was made at 30° C., overnight with aeration (240 rpm). Aliquots or the whole volume were then plated onto selective medium (LB with 4 µg/ml Erythromycin for pG+host9) and were incubated at 28° C. for two days.

The deletion of the B. natto ywfL gene was performed in two separate steps. In the first step (Loop-in) the integration of pMZ66 by homologous recombination (directed by the flanking DNA homologies) was conducted. In the second step (Loop-out) use was made of plasmid replication facilitated excision from the genome and the desired bacterial clones were identified.

Loop-in of pMZ66

The B. natto strain BN1 transformed with the plasmid pMZ66 was inoculated into fresh LB medium supplemented with 2 µg/ml erythromycin and was incubated at 42° C. for 16 hr. This culture was diluted and plated onto on LB plates supplemented with 2 µg/ml erythromycin and incubated at 42° C. At this temperature the pG+Host 9 µplasmid replication protein is no longer active. Consequently, those bacteria, that are selected, are the rare events of plasmid integration at the ywfL gene. This integration is directed by the DNA sequence homology of the ywfL deletion fragment and can occur in either the 5' or 3' homology region. The event of either the 5' or the 3' integration was determined using specifically designed PCR primers on small-scale cultures of the integrants (at 42° C.). This revealed that the majority of the chromosomal integration events occurred at the 5' section of the ywfL gene, with only approximately 10% of events occurring at the 3' end. These clones were confirmed by Southern analysis.

Loop-out of pMZ66

A positive clone with pMZ66 integrated at the 5' end of the ywfL gene was inoculated at 1% into LB medium with 2 µg/ml erythromycin and was incubated at 42° C. for 16 hr. This culture was then used to inoculate at 1% a fresh culture of LB medium and incubated at 28° C. for 16 hr. The culture was diluted, plated onto LB plates and then incubated at 42° C.

The reasoning for proceeding accordingly was as follows: At 28° C. the pG+Host 9 µplasmid replication protein is again active and the reestablishment of replication enhances the excision of the plasmid from the genome, while the final plating and the incubation at 42° C. again shuts-off the pG+Host 9 plasmid replication protein causing the freely replicating plasmid to be lost (no erythromycin selection).

As in the loop-in reaction; the plasmid pMZ66 is considered to have two options for looping out by two distinct routes: (i) by recombination with the same 5' flanking DNA, as with the integration, thus returning to the original parent BN1, or (ii) by recombination with the 3' flanking DNA, that is by incorporating the deletion fragment into the genome and removing the chromosomal ywfL gene with the pG+Host 9 vector.

The resulting colonies incubated at 42° C. showed predominantly large colonies with a few smaller colonies being present. Replica streaking onto LB plates and LB plates supplemented with 2 µg/ml erythromycin determined that all of the small colonies and some of the large colonies tested were erythromycin sensitive.

PCR amplification with primers designed to amplify across the deletion point were used to determine that all the large colonies carried the wild-type BN1 ywfL gene, while the small colonies all contained the designed deletion of the ywfL gene.

The PCR results were confirmed by sequencing the DNA at the deletion point of the ywfL gene, which showed the expected sequence from the constructs. The arrangement of the region around the ywfL gene was confirmed by Southern hybridization and finally it was determined by means of hybridization with that plasmid that no pG+Host 9 vector sequences remained. Five such ywfL deletion strains were identified from independent experiments and named BN10 (I-2077) to BN14.

HPLC Analysis of ywfL Deletions Strains

B. natto strain BN1 and the 5 ywfL deletion strains obtained (BN10 to BN14) were cultured in LB medium for 16 hr at 37° C. The bacteria were removed by filtration through a 0.2 micron filter (Schleicher & Schuell, FP 030/3) and the fatty acids composition was analyzed by HPLC. HPLC was performed on a HPLC Hewlett Packard series 1100 machine using an Arninex Fast Acid 100×7.5 mm column (Bio-Rad, product number 125-0100) stabilized at 40° C. and eluted with 10 mM $H_2SO_4$ at a flow rate of 1 ml/min. Detection was achieved using a HP 1047A Refractometer (Hewlett Packard) also stabilized at 40° C.

The results are presented in Table I, from which it becomes evident that the iso-valeric acids are produced by the fermentation of the bacterium B. natto, and the deletion of the ywfL gene extensively reduces the production of this fermentation product to a minimum.

TABLE 1

Determination of iso-valeric acid levels produced by the BN1 and 5 ywfL deletion derivatives BN10–BN14

| Sample | iso-valeric acid (mg/l) (3-methyl-butyric acid) | iso-valeric acid mmoles/l |
|---|---|---|
| LB medium | 0 | 0 |
| BN1 | 971.7 | 9.51 |
| BN10 | <7.0 | <0.07 |
| BN11 | <7.0 | <0.07 |
| BN12 | <7.0 | <0.07 |
| BN13 | <7.0 | <0.07 |
| BN14 | <7.0 | <0.07 |

EXAMPLES

The following examples illustrate the invention.

Example 1

Preparation of Cubes

According to techniques well known in the art, soybeans were crushed, cooked, and inoculated with spores of the B. natto strain BN10 (I-2077), followed by solid state fermentation (Koji type fermentation) for 2–5 days at 30–50° C. To the resulting fermentation mixture was added a salt brine (NaCl saturated solution). The product was dried, pressed into cubes or was used as the powder for, e.g., bouillon production. The final production did not have the taste common for products containing iso-valeric acids. The novel B. subtilis strain therefore performed equally well in the fermentation of soybeans as compared to commonly used B. subtilis strains.

Example 2 (Comparative)

The same procedure as illustrated in Example 1 was repeated with the proviso of using a wild type B. natto (BN1) for inoculation. The resulting product showed a taste typically for products containing iso-valeric acids.

What is claimed is:

1. A bacterial strain of *B. subtilis*, wherein the ywfl gene, involved in the biosynthesis of iso-valeric acids, has been deleted or is essentially non-functional, such that the strain is essentially devoid of any capability for iso-valeric acid production.

2. The *B. subtilis* strain of claim 1, which is *B. natto* and which does not produce taste perceptible amounts of iso-valeric acids.

3. The *B. subtilis* strain of claim 1, that contains no exogeneous DNA sequences.

4. The *B. subtilis* strain of claim 1, prepared by recombinant gene technology.

5. The *B. subtilis* strain of claim 4, which is *B. natto* I-2077.

6. The *B. subtilis* strain of claim 1, prepared by mutagenesis and selection.

7. A bacterial strain of *B. subtilis*, wherein the ywfl gene, involved in the biosynthesis of iso-valeric acids, has been deleted, such that the strain is essentially devoid of any capability for iso-valeric acid production.

8. The *B. subtilis* strain of claim 7, which is *B. natto* and which does not produce taste perceptible amounts of iso-valeric acids.

9. The *B. subtilis* strain of claim 7, that contains no exogenous DNA sequences.

10. The *B. subtilis* strain of claim 7, prepared by recombinant gene technology.

11. The *B. subtilis* of claim 10, which is *B. natto* I-2077.

12. The *B. subtilis* strain of claim 7, prepared by mutagenesis and selection.

* * * * *